United States Patent [19]

Schmieding

[11] Patent Number: 4,633,869

[45] Date of Patent: Jan. 6, 1987

[54] TENSION RETAINING DEVICE FOR SURGICAL PROCEDURES

[75] Inventor: Reinhold Schmieding, Munich, Fed. Rep. of Germany

[73] Assignee: Arthrex Arthroscopy Instruments, Inc., Norwalk, Conn.

[21] Appl. No.: 813,989

[22] Filed: Dec. 23, 1985

[51] Int. Cl.[4] .............................................. A61B 17/00
[52] U.S. Cl. .................................. 128/303 R; 128/321; 128/346
[58] Field of Search ................ 128/3, 303 R, 321, 346

[56] References Cited

U.S. PATENT DOCUMENTS

| 2,397,823 | 4/1946 | Walter | 128/321 |
| 3,452,740 | 7/1969 | Muller | 128/303 R |
| 3,822,697 | 7/1974 | Komiya | 128/3 |
| 3,877,433 | 4/1975 | Librach | 128/303 R |

FOREIGN PATENT DOCUMENTS

| 2558570 | 7/1976 | Fed. Rep. of Germany | 128/321 |
| 2816961 | 2/1979 | Fed. Rep. of Germany | 128/346 |

Primary Examiner—Albert J. Makay
Assistant Examiner—Steven E. Warner
Attorney, Agent, or Firm—John K. Conant

[57] ABSTRACT

The device includes a pair of rollers through oppositely disposed notches through the wall of a tubular section to engage opposite sides of the shaft of a surgical instrument that is through the bore of the tubular section. The tubular section is slideable in a sleeve element and the ends of the rollers are rotatably received in the respective slots of two pairs of slots in the walls of the sleeve element. A pad removably mounted on one end of the sleeve element has a central opening for the instrument shaft to pass through. The pairs of slots converge in the direction of the end of the sleeve element on which the pad is mounted to a distance apart not less than the distance between the bottoms of the notches in the tubular section. Releasable spring means urge the rollers toward the converging ends of the pairs of slots so that the shaft of the instrument may be drawn out through the device in the direction in which the slot pairs diverge, but not in the opposite direction in which they converge, unless the spring means releases it. The device is used in combination with a surgical instrument for procedures in which the instrument engages material within a body and is drawn out to stretch the material outward under tension. The device grips the instrument to retain the tension until the release mechanism is actuated.

9 Claims, 4 Drawing Figures

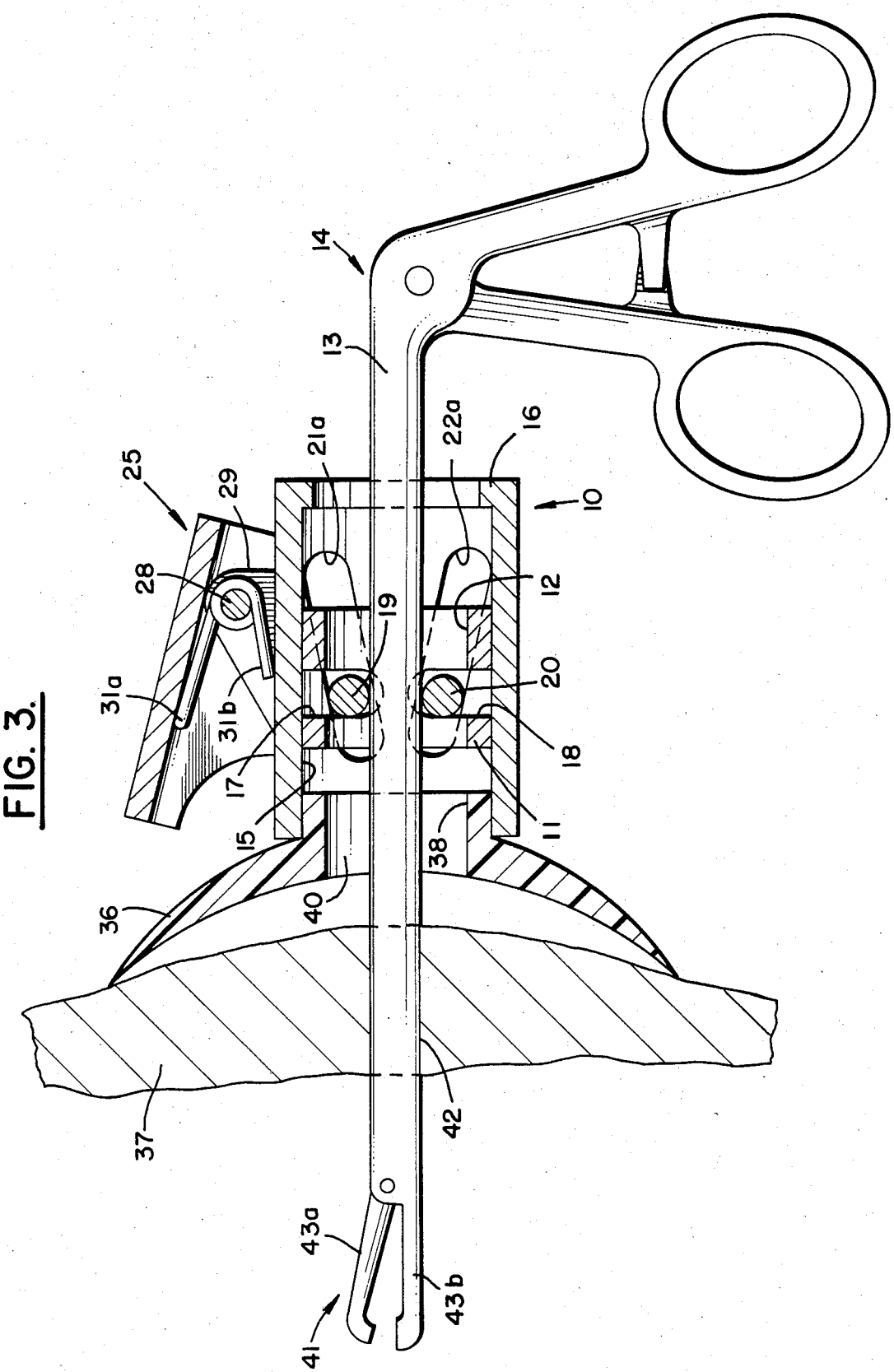

TENSION RETAINING DEVICE FOR SURGICAL PROCEDURES

BACKGROUND AND SUMMARY OF THE INVENTION

The present invention is a releasable one way clutch type tension retaining device for use in surgical procedures, such as arthroscopy, for example, wherein an instrument which has a shaft portion and a working end is inserted through a body surface to engage and stretch under tension material, such as cartiledge, muscle or fatty tissue, for example, either to hold the material to be worked on by another instrument or to hold the material away from underlying material that is to be worked on. The instrument applies tension to the material by being drawn outward from the body.

The device of this invention is adapted for use with a number of different surgical instruments in a variety of surgical procedures. For example, it is particularly adapted for use with different types of grasping forceps for retaining tension during knife cutting or shaving procedures. It is also used with fat pad retractors for holding pads of fat out of the way for cutting, shaving or suturing in areas under the fat pad. It has also been used to hold a retrograde marking hook in position during arthroscopic reconstruction.

The device includes a tubular section through the bore of which the shaft of a surgical instrument is received. The tubular section is slideably received within the bore of a sleeve element and a one way type of clutch mechanism is provided by at least one roller through and movable up and down in a notch that is in the wall of the tubular section. The notch is across the axis of the tubular section and opens into its bore. The notch is of a depth such that the space between the the roller resting in the bottom of the notch and an opposite surface, which may be the opposite wall of the bore of the tumular section or, preferably, another roller in another notch through the opposite side of the tubular section, is less than the diameter of the shaft of an instrument that is to be used with the device.

The ends of the roller, or rollers, are rotatably received respectively in slots in opposite walls portions of the bore of the sleeve element. The slots extend generally longitudinally of the bore of the sleeve element, but at an angle with respect to the axis of the bore so that the plane of the slots converges toward the opposite wall of the sleeve element bore in one direction and diverge from it in the opposite direction. Thus when the notched tubular section is moved within the sleeve element relatively in the direction in which the plane of the slots converges toward the opposite surface within the sleeve element the notch carries the roller toward that opposite surface, and hence toward the opposite surface within the bore of the tubular section. The latter surface may be the opposite wall of the bore of the tubular section or, in the preferred form, the surface of another roller in another, oppositely disposed notch in the opposite wall of the tubular section, the end portions of this other roller being received in another pair of slots in the walls of the sleeve element. The plane of such a second pair of slots would converge toward the opposite wall of the sleeve element in the same direction as the plane of the first pair of slots and at the same longitudinal location relative to the length of the sleeve element.

In any case the relative movement of the tubular section within the sleeve element in the slot converging direction causes the roller or rollers to pinch an instrument shaft that is through the bore of the tubular section between it and the opposite surface, which is either the bore wall or another roller.

Spring means is connected to urge the parts in relative directions in which the roller, or rollers, are urged into instrument shaft gripping position. Thus an instrument whose shaft is through the bore of the tubular section is prevented from being drawn further through the tubular section in the converging direction of the slots by the pinching action of the roller or rollers, but may be drawn in the opposite direction, the direction in which the slots diverge.

The spring means is releasable to enable an instrument shaft to be moved freely through the bore of the tubular section in either direction when desired. In a preferred form of the device of this invention the spring means is a spring loaded lever pivotted on the sleeve element and having an arm connected to an end of the roller, or to one of the rollers, if there are two, to urge the roller in the converging direction.

A broad circular pad is mounted on the end of the sleeve element toward which the plane, or planes, of the slots therein converge toward the opposite side of its bore. This pad is removable and replaceable for hygenic purposes and is adapted to bear against the surface of the body against which the device is placed in use in order to distribute the load exerted by the device on the body surface and thus cushion the device.

With the device placed with its pad against a body surface the shaft of a surgical instrument, such as grasping forceps, is through the tubular section and the working end of the instrument, e.g. the jaws of grasping forceps, projects through the body surface to the inside of the body where it is applied to grip or hook onto material—tissue, muscle or cartiledge, for example—within the body. The instrument is then drawn outward through the device is stretch or pull the material outward to the desired degree of tension. The slots, notch and roller clutch mechanism then operates to hold the instrument and the material held by it in the desired position by means of the tension created by the stretched material pulling inward on the instrument. The device then maintains the instrument in the tension position and frees the hands of the doctor or nurse for other work. When the work is completed the tension is relieved to allow the instrument to be move inward to detach it from the material in the body and then withdraw if from the body, by actuating the spring means to release the grip of the roller, or rollers, on the instrument shaft.

DESCRIPTION OF THE DRAWINGS

Further features, objects and advantages of the tension retaining device of this invention will be apparent from the following detailed description of an illustrative embodiment of the device shown in the accompanying drawings in which:

FIG. 3 is a longitudinal section through the device of FIG. 1 showing it in use with a grasping forcep.

DETAILED DESCRIPTION

Figure 1:
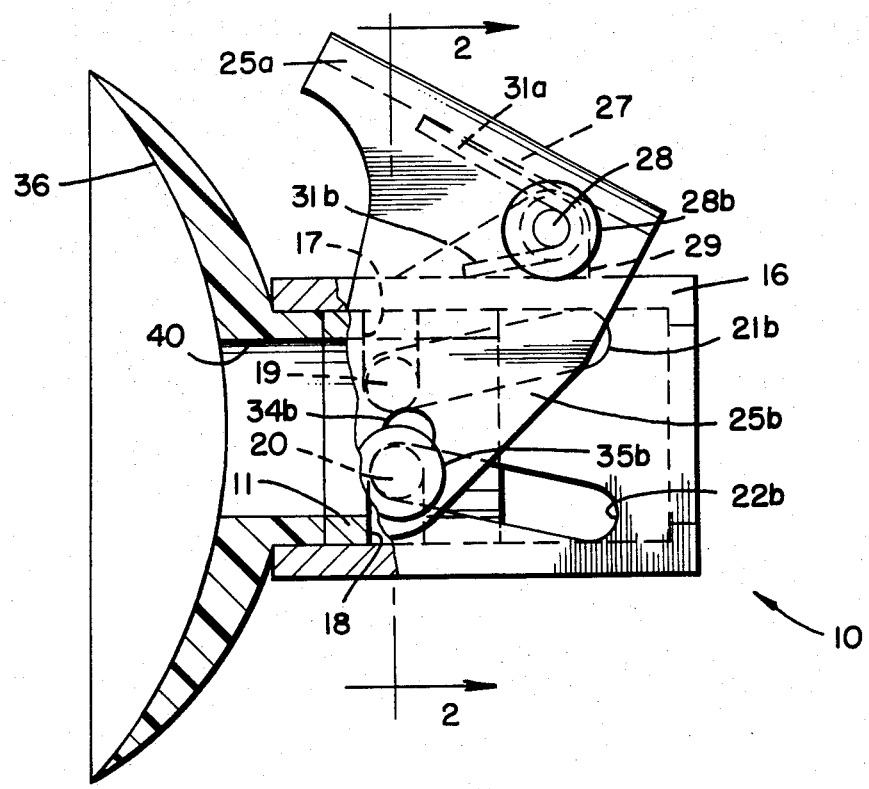
FIG. 1 is a side view, partly in section, of the tension retaining device of the invention.

Referring now to the drawings a preferred form of the tension retaining device 10 of this invention is provided by an open ended tubular section 11 which has a bore 12 that is dimensioned for a shaft 13 of a surgical instrument 14, such as a graping forcep as illustrated in FIG. 3, to pass through.

The tubular section 11 is slideably received within the bore 15 of a sleeve element 16 and has a pair of notches 17 and 18 respectively in opposite sides and opening into its bore 12. The notches 17, 18 are opposite each other in alignment across the bore and are of depths such that their bottoms are apart a distance less than the diameter of the shaft 13 of an instrument with which the device 10 is intended to be used.

The notches 17,18 each have a roller, rollers 19 and 20 respectively, received through them. The ends of the rollers 19, 20 are rotatably received in pairs of slots 21a, 21b and 22a, 22b, respectively, that are in the walls of the sleeve element 16. The slots 21a, 21b and 22a, 22b of each pair are in alignment with each other at opposite sides of the bore 15 of the sleeve element 16. The lengths of the slots are angularly disposed relative to the axis of the bore 15 so that the plane of each of the pairs of the slots converges toward the opposite in one direction, and diverges therefrom in the opposite direction. As indicated in FIGS. 1 and 3 the planes of the pairs of slots 21a, 21b and 22a, 22b converge to a distance apart less than the diameter of the shaft 13 of an instrument with which the device is to be used. Also the tubular section 11 is axially positioned within the sleeve element 16 so that the notches 17, 18 are adjacent to the slots as necessary for the ends of the rollers 19,20 through the notches to be received in the slots. Thus, when the tubular section 11 is moved longitudinally within the bore 15 of the sleeve element 16 in the direction in which the slot pairs 21a,21b and 22a, 22b converge, i.e. to the left in FIGS. 1 and 3 the rollers 19, 20 being carried by the notches 17, 18 are moved along in the respective slot pairs 21a, 21b and 22a, 22b to converge and bear against and grip the shaft 13 of an instrument that is through the bore 12 of the tubular section 12. As the shaft 13 or the tubular section 11 move relatively in the slots converging direction the grip of the rollers on the shaft increases to the point at which further movement of the shaft in that direction is prevented. On the other hand movement of the shaft 13 or the tubular section 11 relatively in the opposite, slot diverging, direction, to the right in FIG. 3, causes the rollers to diverge and release their grip on the shaft 13 and permit free movement of the shaft in that direction.

Figure 2:
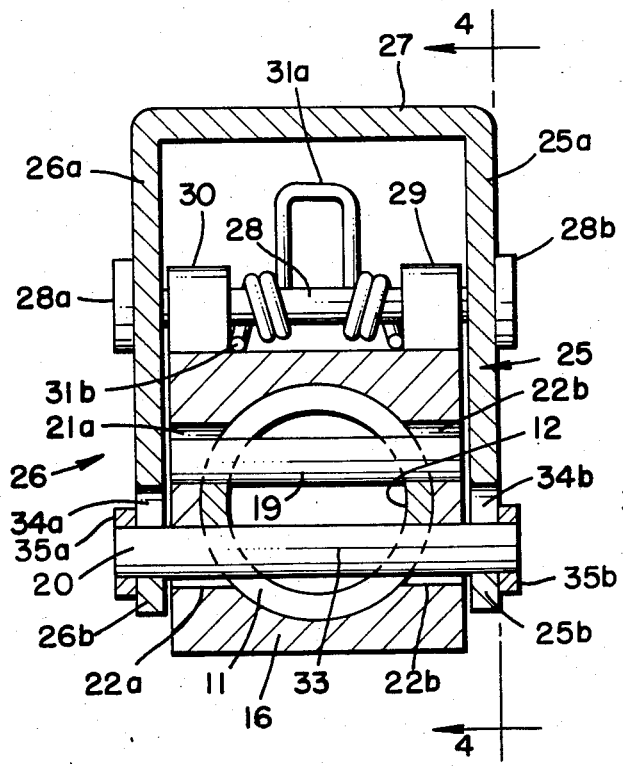
FIG. 2 is a section along the line 2—2 of FIG. 1.

The tubular section 11 is resiliently urged in the slots converging direction, in which it carries the rollers 19, 20 toward the converging ends of the slot pairs by spring means illustrated in FIGS. 1 and 2. An aligned pair of L shaped levers 25, 26 consisting of lever arms 25a, 25b and 26a, 26b are at opposite sides of the sleeve element 16 and are joined together as a unit by a web 27 between the arms 25a, 26a, which are the top arms of the levers, across the top of the sleeve element The levers 25, 26 are pivotally mounted on the sleeve element 16 by a shaft 28 through the elbow of the levers 25, 26 and journalled through a pair of posts 29, 30 projecting upward from opposite edges of the sleeve element 16. The shaft 28 is held in place through the posts and levers by caps 28a, 28b pinned on the outer ends of the shaft 28, respectively.

Figure 4:
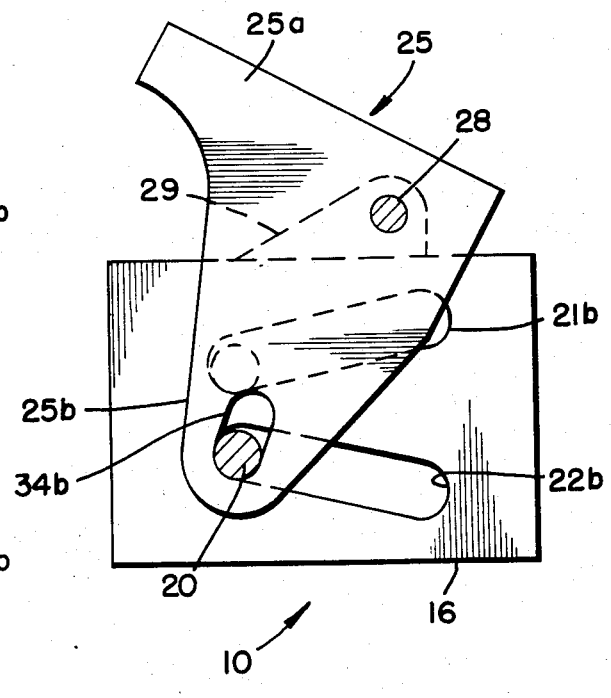
FIG. 4 is a view along the line 4—4 of FIG. 2

The levers 25, 26 are resiliently urged to pivot in the clockwise direction, as viewed in FIGS. 1 and 4, by a coil spring 31 around the shaft 28 with one tail end 31a projecting under and bearing against the web 27 which joins the levers 25 and 26. The other tail end 31b of the coil spring 31 extends over and bears down against the top of the sleeve element 16.

The lower ends of the lever arms 25b, 26b are loosely connected to the lower roller 20 by the ends of the roller 20 extending through slots 34a, 34b in the lower end portions of the lever arms 25b, 26b. Caps 35a, 35b on the ends of the roller 20 hold the roller in place.

The slots 34a, 34b in the lever arms 25b, 26b extend radially of the pivot point of the levers 25, 26 defined by the 28, and are made a sufficient radial length to permit the ends of the roller 20 move freely up and down therein as the levers 25, 26 swing about the the shaft 28. Thus when the levers 25, 26 are pivotted the lever arms 25b, 26b move the roller 20 along in the pair of slots 22a, 22b, which are straight.

When the levers 25, 26 pivot about the shaft 28 they, acting through the roller 20, cause the roller 20 to move along in the pair of slots 22a, 22b and bear against sides of the notch 18 in the tubular section 11 and thereby move the tubualar section longitudinally in the bore 15 of the sleeve element 16. This causes the rollers 19 and 20 to converge or diverge, depending upon the direction of movement. As shown the spring 31 is arranged and biased to cause the levers 25, 26 to swing in the clockwise direction as viewed in the drawings. When the levers thus swing in the clockwise direction they cause the rollers 19, 20 to converge and grip a shaft 13 that is between them.

To release the spring pressure, and hence release the grip of the rollers 19, 20 on a shaft 13, the levers are moved in the opposite, counterclockwise, direction by pressing down on the web 27 that is between the tops of the levers 25, 26. This causes the lower arms 25b, 26b of the levers 25, 26, acting through the roller 20, to move the tubular section 11 to the right, as viewed in the drawings, in the direction in which the slots diverge, so that the rollers 19,20 are caused to diverge away from a shaft 13 between them therby releaseing the shaft to be moved in either direction through the bore 15 of the tubular section 11 of the device.

The end of the sleeve element 16 toward which the lots 21a, 21b and 22a, 22b converge—the left end as viewed in FIGS. 1 and 3—has a resilient dish shaped pad 36 removably mounted on it to bear against a surface 37 of a body which is to undergo a surgical procedure. The pad 36 has a larger circumference than the end of the sleeve element and thus provides a cushion that distributes the pressure of the device 10 over a relatively large area of the body surface 37 when the device is in use. The pad 36, which is suitably made of PVC, is removably mounted on the sleeve element by a boss portion 38 of the pad frictionally received in the end portion of the bore 15 of the sleeve element. Thus the pad 36 can be removed from the device for sterilization. The center of the pad 36 has an opening through it into the bore 15 to permit a shaft 13 and the working end 41 of a surgical instrument with which the device is to be used to pass through the device to be inserted into a body for a surgical procedure.

In use the device 10 is placed with its pad 36 against an area of a patient's body surface through which the working end 41 of a surgical instrument, such as a grasping forcep as shown in FIG. 3, is to be inserted.

The levers 25, 26 are rotated by pressing down the web 27 which connects them at the top to cause the rollers 19, 20 to move apart and let the shaft 13 of a surgical instrument 14 pass through into the interior of the patient's body. The instrument passes into the patient's body through an opening 42 previously made in the body surface by another instrument or by the instrument with which the device 10 is being used. With the rollers 19, 20 held apart by depressing the web 27 the instrument inserted into the patient's body can be moved back and forth as necessary to bring the instrument's working end 41 into position to engage material within the body for drawing the material outward toward the surface 37 to a position in which the performance of the surgical procedure is facilitated. When the working end of the instrument, and the material engaged thereby, have been moved outward to the desired position the levers 25, 26 are released, by letting up on the web 27, so that the rollers 19, 20 are moved to the converging ends of the slots 21a, 21b and 22a, 22b and thus grip the shaft 13 under the pressure exertd by the coil spring 31. This pressure of the rollers 19, 20 holds the shaft 13 so that it can not move further inward but can be drawn outward.

The instrument 14 illustrated in FIG. 3 is a grasping forcep whose working end 41 is a pair of jaws 43a, 43b which grip the material (not shown) within the body. With the jaws 43a, 43b gripping material, such as cartilage, muscle or a fat pad, for example, the instrument is drawn outward through the device 10—to the right as viewed in FIG. 3—until the material is stretched outward the desired amount. The gripped material which is thus drawn outward under tension applies inwardly directed tension on the instrument, drawing the shaft 13 of the instrument inward throught the tubular section 11—to the left as viewed in FIG. 3—against the one way clutch action of the rollers 19, 20 produced by the cooperation of the coil spring 31 and the converging slots 21a, 21b and 22a, 22b in which the rollers move. The shaft 13 is thus retained in its tensioned position, holding the material engaged by the working end of the instrument stretched outward, for as long as necessary for the procedure being performed. To release the grip of the instrument on the material and remove the instrument from the body, the levers 25, 26 are rotated against the bias of the coil spring 31 by pressing the web 27 which joins the tops of the levers. This releases the spring pressure from the rollers and moves them apart from the shaft of the instrument 14. The instrument is then free to be moved in and/or out as necessary to free its working end from engagement with the body material and then to be withdrawn from the body and out through the device 10.

What is claimed is:

1. A tension retaining device for use in surgical procedures in which the working end of an instrument which has a shaft portion is inserted through a surface of a person's body to engage material within the body for drawing and holding the material outward toward said surface under tension, comprising in combination:

an open ended tubular section concentrically received within the bore of an open ended sleeve element and slideable therein, said tubular section having a bore of sufficient diameter for the shaft of an instrument to be slideably received therethrough, one end of said sleeve element being adapted to bear against a surface of a person's body, said tubular section having a notch diametrically through one wall and opening into its bore, a surface in the bore of said tubular section at the opposite side of said bore from said notch, a cylindrical roller extending axially through said notch, the relative dimensions of said notch and said roller being such that with the roller resting in the bottom of the notch the space between the roller and said opposite surface in the bore of said tubular section is less than the diameter of the shaft of an instrument that is to be received through said tubular section.

said sleeve element having a pair of slots respectively in alignment through opposite side walls thereof and opening into its bore with the respective end portions of said roller rotatably received in said slots, said slots extending generally longitudinally of the bore of said sleeve element at an angle to the axis of said bore such that by relative movement of said tubular element longitudinally within the sleeve element the walls of the slots acting on said roller end portions cause the roller to move relatively down and up in said notch, depending upon the direction of relative movement, said roller being moved down in said notch, toward said opposite surface, by movement of said tubular element in a first direction, toward the end of said sleeve element that is adapted to bear against a surface of a person's body and being moved up in said notch, away from said opposite surface, by relative movement in the opposite direction, means resiliently urging said tubular element in said first direction and thereby resiliently urging said roller toward said opposite surface so that a said instrument whose shaft is through the bore of said tubular section is permitted by the angular disposition of said slots to be moved longitudinally in the direction away from the end of said sleeve element that is adapted to bear against a surface of a person's body, but is prevented from movement in the opposite direction, and means actuatable to counteract said resiliently urging means and thereby permit a said instrument to be moved in said opposite direction.

2. The tension retaining device of claim 1 in which said surface in the bore of said tubular section at the opposite side of said bore from said notch is a second roller generally parallel to the first said roller and rotatably mounted through the walls of said tubular section.

3. The tension retaining device of claim 1 in which said means resiliently urging said tubular element in said first direction and said means actuatable to counteract said resiliently urging means comprise:

a lever pivotally mounted on said sleeve element, an end of said roller extending outward of said sleeve element through one of said slots in said sleeve element, said lever having an elongated slot through one end portion and mounted with its said slot receiving said end of the roller therethrough, said lever and its said slot being disposed for causing said roller to be moved back and forth in the said slots in said sleeve element when said lever is swung back and forth about its pivot point, and a spring engaging said lever to resiliently urge the lever to pivot in the direction in which the lever urges said roller to move toward the end of said sleeve element in which the roller is moved toward said opposite surface in the bore of said tubular section.

4. The tension retaining device of claim 1 in which said end of said sleeve element that is adapted to bear against a surface of a person's body has a resilient pad removably mounted on it, said pad having a central opening therethrough opening into the bore of said sleeve element for the shaft of an instrument to pass through.

5. The tension retaining element of claim 4 in which the diameter of said pad is greater than the diameter of said sleeve element.

6. A tension retaining device for use in surgical procedures in which the working end of an instrument which has a shaft portion is inserted through a surface of a person's body to engage material wihtin the body for drawing and holding the material outward toward said surface under tension, comprising in combinaation:

an open ended tubualr section concentrically received within the bore of an open ended sleeve element and slideable therein, said tubular section having a bore of sufficient diameter for the shaft on an instrument to be slideably received therethrough, one end of said sleeve element being adapted to bear against a surface of a person's body, said tubular section having a pair of notches respectively through opposite side walls thereof diametrically across the axis of the bore of said section and opening into said bore, a pair of cylindrical rollers received respectively in and extending axially through said notches, the relative dimensions of said notches and said rollers being such that with the rollers resting in the bottoms of the notches the space between the rollers is less than the diameter of the shaft of an instrument that is to be received through said tubular section, said sleeve element having two pairs of slots opening through its walls and into its bore, the slots of each pair being in alignment at opposite sides of said bore and extending generally longitudinally of said bore, the pairs of slots being respectively at opposite sides of the axis of said bore and converging toward each other in the direction toward the end of said sleeve element that is adapted to bear against a person's body, the end portions of said rollers being rotatably received respectively in said aligned pairs of slots in said sleeve element, the converging ends of said pairs of slots converging to a distance apart at least as narrow as the space between said rollers with the rollers resting in the bottoms of said notches, whereby relative movement of said tubular section longitudinally within said sleeve element causes the rollers to move in said notches relatively toward and away from each other, depending upon the direction of relative movement of the tubular section and sleeve element, said rollers being moved toward each other by movement of said tubular element in a first direction, toward the end of said sleeve element that is adapted to bear against a surface of a person's body, means resiliently urging said tubular element in said first direction so that a said instrument whose shaft is through the bore of said tubular section is permitted by the angular disposition of said pairs of slots to be moved longitudinally in the direction away from the end of said sleeve element that is adapted to bear against a surface of a person's body, but is prevented from movement in the opposite direction, and means actuatable to counteract said resiliently urging means and thereby permit a said instrument to be moved in said opposite direction.

7. The tension retaining device of claim 6 in which said means resiliently urging said tubular element in said first direction and said means actuatable to counteract said resiliently urging means comprise:

a pair of generally L shaped parallel levers with the levers being respectively at opposite sides of said sleeve element and being pivotally mounted to pivot in planes parallel to the axes of the bores of said sleeve element and tubular section and a right angles to the axis of one of said rollers, said pivot point being spaced to one side of the axes of said sleeve element and tubular section and at the side opposite the side of said axes from said axis of said one of said rollers, and from the one pair of said pairs of slots through which said one roller is received, corresponding lever arms of said pair of levers having elongated slots in their end portions generally radially disposed to the pivot points of said levers, said one roller having its end portions rotatably received in said elongated slots in said lever arms so as to be moved back and forth along in the pair of slots in said sleeve element in which said one roller is received, and hence be moved up and down in the corresponding one of said notches, by pivotal movement of said levers, the corresponding one s of other lever arms of said levers being joined so that the levers move in unison, and spring means operatively engaging said levers to resiliently urge the levers to pivot in the direction in which the ones on said lever arms that have said elongated slots therein push said one roller, that is received in said elongated slots, toward the converging ends of said paairs of slots in said sleeve element.

8. The tension retaining device of claim 6 in which said end of said sleeve element that is adapted to bear against a surface of a person's body has a resilient pad removably mounted on it, said pad having a central opening therethrough opening into the bore of said sleeve element for the shaft of an instrument to pass through.

9. The tension retaining device of claim 8 in which the diameter of said pad is greater than the diameter of said sleeve element.

* * * * *